United States Patent [19]

Tankovich

[11] Patent Number: 5,226,907
[45] Date of Patent: Jul. 13, 1993

[54] HAIR REMOVAL DEVICE AND METHOD

[76] Inventor: Nikolai I. Tankovich, 3957 Nobel Dr. Apt. 244, San Diego, Calif. 92122

[21] Appl. No.: 783,789

[22] Filed: Oct. 29, 1991

[51] Int. Cl.$^5$ ............................................. A45D 26/00
[52] U.S. Cl. .................................. 606/133; 606/131; 606/9
[58] Field of Search .................... 128/395, 398; 606/1, 606/15, 9, 16, 36, 43, 131, 133

[56] References Cited

U.S. PATENT DOCUMENTS

| | | | |
|---|---|---|---|
| 3,538,919 | 11/1970 | Mayer | 128/398 |
| 3,693,623 | 9/1972 | Harte et al. | 606/3 |
| 3,769,963 | 11/1973 | Goldman et al. | 606/3 |
| 3,794,028 | 2/1974 | Mueller et al. | 606/133 |
| 3,834,391 | 9/1974 | Block | 128/398 |
| 4,336,809 | 6/1982 | Clark | 128/398 |
| 4,388,924 | 6/1983 | Weissman . | |
| 4,608,978 | 9/1986 | Rohr | 606/9 |
| 4,617,926 | 10/1986 | Sutton . | |
| 4,813,412 | 3/1989 | Yamazaki et al. | 606/46 |
| 5,059,192 | 10/1991 | Zaias | 606/9 |

FOREIGN PATENT DOCUMENTS

| | | | |
|---|---|---|---|
| 1041610 | 10/1978 | Canada | 606/9 |
| 3220962 | 12/1983 | Fed. Rep. of Germany | 606/9 |
| 2590791 | 6/1987 | France | 606/9 |
| 2595239 | 9/1987 | France | 606/43 |
| 8002640 | 12/1980 | World Int. Prop. O. | 606/43 |
| 8602783 | 5/1986 | World Int. Prop. O. | 606/9 |

OTHER PUBLICATIONS

Porphyrins In Tumor Phototherapy–Alessandra Andreoni et al.–May 16, 1983 pp. 143–155.
Investigation and Therapy In Dermatology With Dye Lasers A. Anders et al Jun. 20, 1977-pp. 520–526.

*Primary Examiner*—Stephen C. Pellegrino
*Assistant Examiner*—Colenn Dawson
*Attorney, Agent, or Firm*—John R. Ross

[57] ABSTRACT

The present invention provides a device and process for the permanent removal and of unwanted human hair. Hair on a section of skin is contaminated with a substance having high absorption of a frequency band of light which passes through the surface of the skin. The skin is illuminated with light at this frequency band at sufficient intensity and duration to kill the follicles of the hair. Specific embodiments to produce death of the follicles by heating and by photochemical reaction.

4 Claims, 5 Drawing Sheets

# HAIR REMOVAL DEVICE AND METHOD

This invention relates to devices and methods for hair removal and in particular to the use of laser devices for hair removal.

BACKGROUND OF THE INVENTION

The principal methods presently used for hair removal involve the use of electrolysis techniques or chemical depilatories. These techniques involve some pain, are time consuming, and demand a fair degree of expertise in their application and normally do not guarantee a permanent effect.

The prior art of hair removal also includes attempts at removing hair with laser beams. Three such techniques are described in the following United States patents: Weissman et al., Method for Laser Depilation Device and Method, U.S. Pat. No. 4,388,924; Sutton, Depilation Device and Method, U.S. Pat. No. 4,617,926; and Mayer, Depilation by Means of Laser Energy, U.S. Pat. No. 3,538,919. All of these devices and methods teach the removal of hairs one hair at a time with a narrowly focused laser beam. Therefore, they are relatively inefficient and time consuming.

What is needed is a simple, harmless device and method for removal of hair over a relatively broad area of skin.

SUMMARY OF THE INVENTION

Present invention provides a device and process for the permanent removal of unwanted human hair. Hair on a section of skin is contaminated with a substance having high absorption of a frequency band of light which passes through the surface of the skin. The skin is illuminated with light at this frequency band at sufficient intensity and duration to kill the follicles of the hair. Specific embodiments produce death of the follicles by heating and by photochemical reaction.

DETAILED DESCRIPTION OF PREFERRED EMBODIMENTS

Preferred embodiments of the present invention can be described by reference to the figures.

Coat and Heat Method

Figure 1:
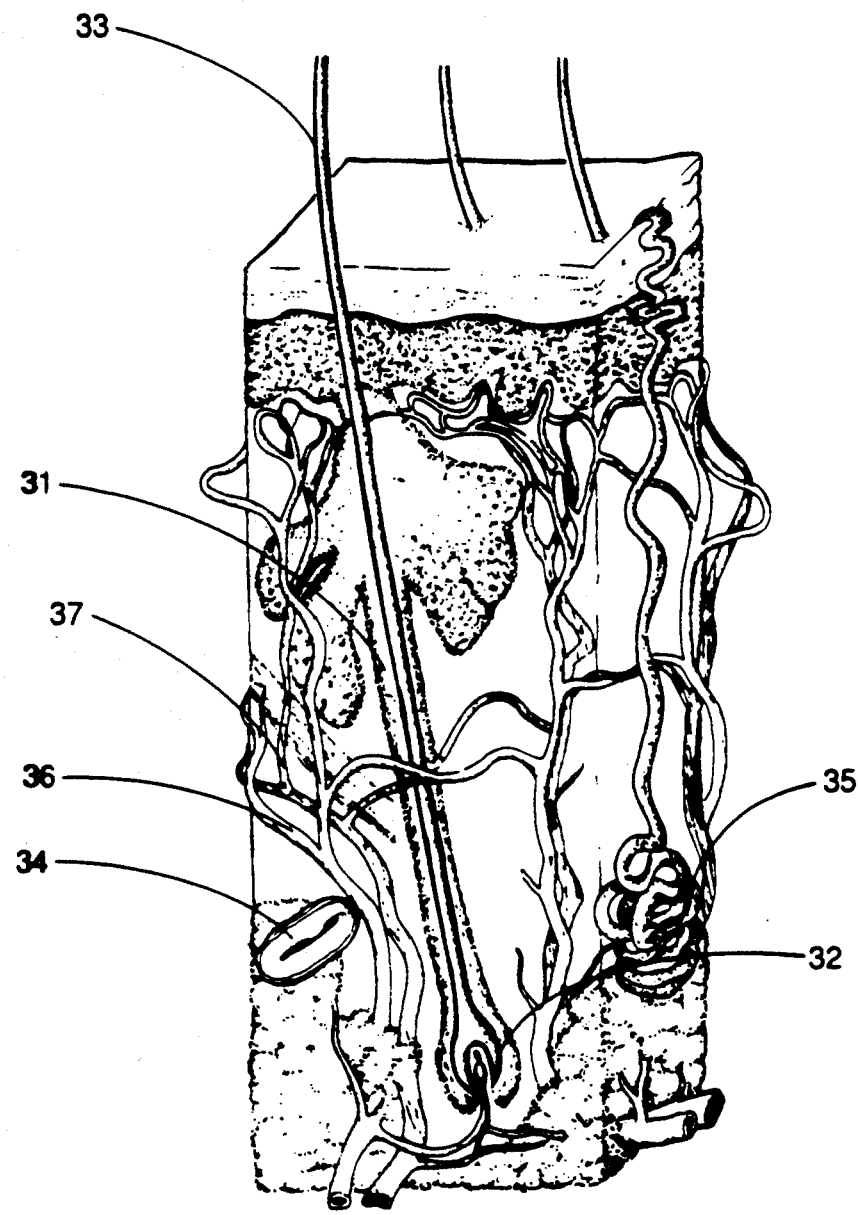
FIG. 1 is a drawing of a section of human skin showing a growing hair.

A section of human skin showing a cross section of one hair is shown in FIG. 1. A first preferred embodiment of the present invention can be described by reference to FIGS. 2-4. FIG. 1 shows the hair shaft 33 a nerve ending 34, a sweat gland 35 and arteries 36 and veins 37. First, a laser absorbing carbon suspension is prepared of carbon powder in peach oil. The particle size of the powder preferably is about 10-20 nm and its concentration preferably is about 15% to 20% by volume.

Figure 2A:
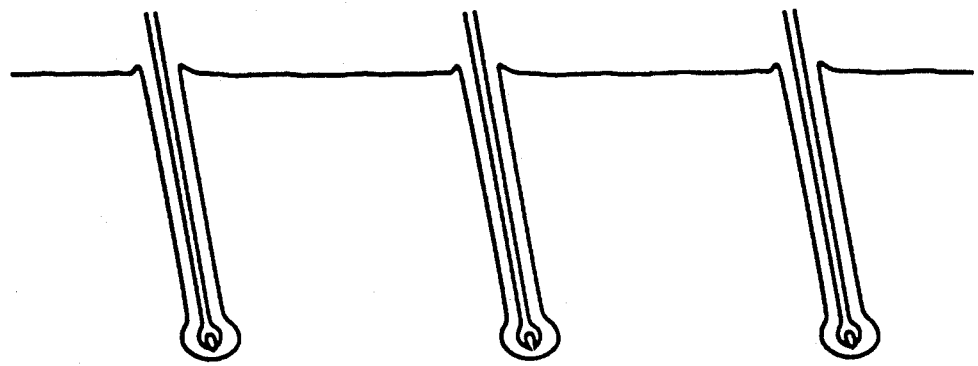
FIGS. 2A, B and C show a cross section of skin and 3 hairs during 3 stages of a process of one embodiment of the present invention.
Figure 2B:
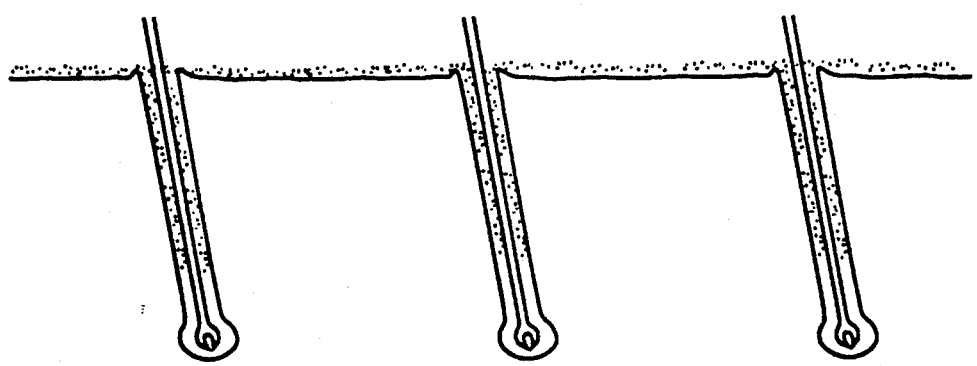
Figure 2C:
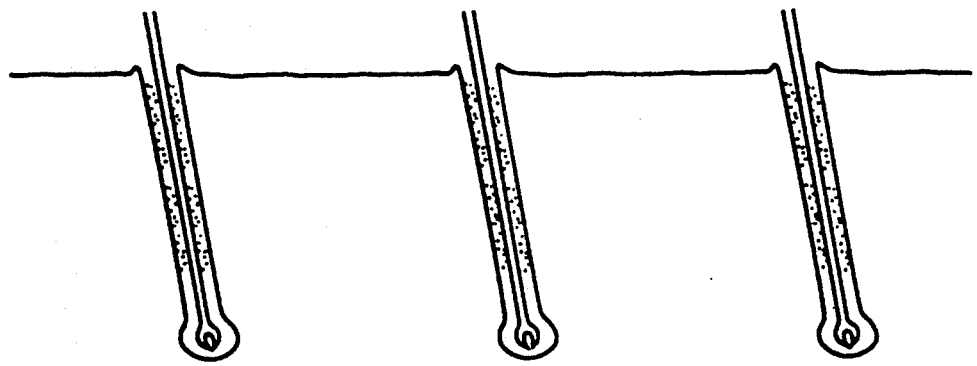

A clean section of skin is depicted in FIG. 2A. This suspension is rubbed on the skin with a massaging action so that portions of the carbon suspension infiltrates the hair ducts of the hair that is be removed as shown in FIG. 2B. Next to the surface of the skin is cleaned preferably with an alcohol pad to make the skin surface clean but to leave the hair pores contaminated with the carbon suspension as shown in FIG. 2C.

Laser Application

The laser device used in this preferred embodiment is a $CO_2$ pulse laser which has the spikes in the range of 10.6 microns. Light in this range will pass through the surface of the skin of a fair skin person and is readily absorbed in carbon. Laser parameters such as pulse width and repetition rate can be selected to best fit the skin and hair types of the patients. The parameter for two specific examples which I have utilized with good results for hair removal are shown in Table 1:

TABLE 1

| | Parameters Preferred. | |
|---|---|---|
| | First Example | Second Example |
| Pulse Width | 275 ns | 200 $\mu$s |
| Repetition Rate | 30 Hz | 8 Hz |
| Laser Spot Size | 1 cm$^2$ | 1 cm$^2$ |
| Energy per Pulse | 0.1 Joule | 0.2 Joule |
| Scanning Rate | 20 seconds per 10 cm$^2$ | 30 seconds per 10 cm$^2$ |

Each point on the skin receives illumination for about 2 seconds and about 60 pulses and each square centimeter receives about 6 Joules. Some of the light is reflected. I estimate that of the light which is not reflected about 50 to 80 percent of the energy of each pulse is absorbed in the carbon.

Figure 3:
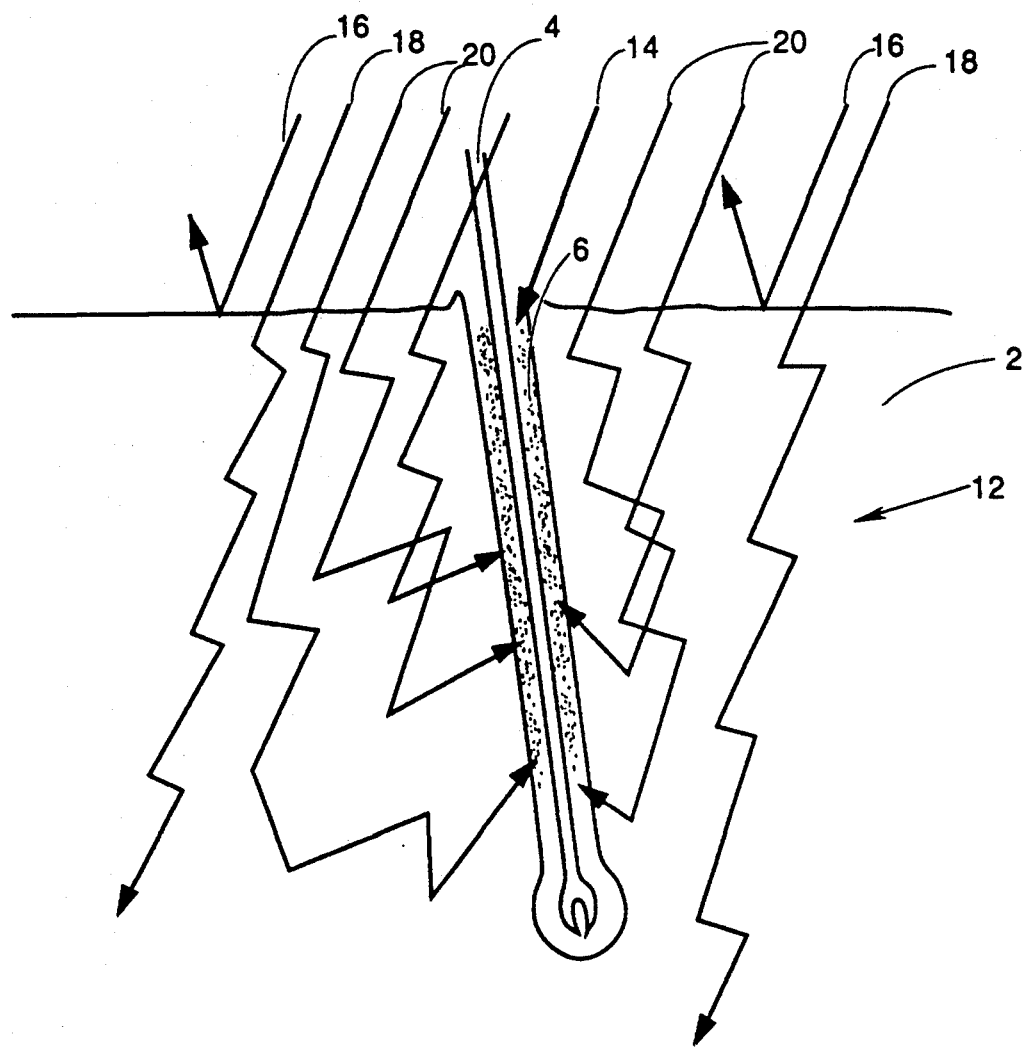
FIG. 3 shows qualitively the paths of the photons of a laser pulse showing absorption in a carbon-oil suspension.

FIG. 3 shows a simplified view of a section of human skin and qualitatively the paths 12 of some of the photons of a laser pulse illuminating a section of skin 2 containing a hair duct with a hair 4 contaminated with carbon suspension 6. A few of the photons travel directly through the skin and are absorbed in the carbon (depicted by photon 14). Some are reflected from the skin surface (depicted by photons 16). Some are absorbed in the skin (depicted as photons 18) but a major portion of the photons (I estimate 50-80 percent) undergo diffuse reflectance in the skin and are absorbed in the carbon after several reflections.

Operating within the parameters specified is very important. They have been chosen to preferentially heat the suspension which in turns heats the hair follicles and the blood vessels feeding the follicles to temperatures high enough to kill the hair follicles and the tissue feeding the follicles but to minimize the heat to the rest of the skin tissue. The pulse width is a most important parameter. It must be chosen so that a large amount of energy is deposited in the suspension quickly so that the temperature of the suspension rises rapidly in steps to about above 70°-80° C. This temperature applied for about 1 to 3 seconds is high enough to kill the follicles and/or the vessels feeding the follicles but not high enough to vaporize the oil. During this short period minimal heat is transferred to the skin tissue except that tissue immediately surrounding the follicle.

I have performed hair removal experiments using the parameters shown in Table 2 with excellent results.

There is no significant pain. The hair is permanently removed and there is no apparent detrimental effect.

I have performed a qualitative mathematical analysis in order to estimate heat absorption and temperature distribution in the hair and skin tissue. This analysis is shown in Table 3.

TABLE 2

Heating of hair and carbon oil suspension in hair duct.

| | |
|---|---|
| Repetition Rate | 33 pulses per second |
| Time between pulses | about 0.03 seconds |
| Hair duct diameter | 0.1 mm |
| Energy per Pulse | 0.1 J |
| Energy per second | (0.1 J) (33) = 33 J/sec = 3 W |
| Beam spot | 1 cm$^2$ |
| Hair spacing | 130 hairs/cm$^2$ |
| Distance between hairs | 0.1 cm = 1 mm |
| Assume ¼ of energy goes into hair duct | |
| Energy per hair per pulse | (0.1 J/130)/4 = 0.00016 J |
| Volume of hair duct | |
| Length 1 mm | |
| Diameter 0.1 mm | |
| Vol. $= 1 \pi \left(\frac{D}{2}\right)^2 =$ | $(0.1 \text{ cm}) \pi \left(\frac{0.01}{2}\right)^2 = 0.0000078 \text{ cm}^3$ |
| Density of oil and hair = | 0.9 gm/cm$^3$ |
| Mass of oil & hair | 0.000007 gm |
| Specific heat of oil & hair assume | 4 J/gm °C. |
| Temperature rise per pulse, $\Delta T = \frac{Q}{mc}$ | $\frac{0.00016 \text{ J}}{(0.000007 \text{ gm})4\text{J/gm °C.}} \approx 5° \text{ C.}$ |

Thus, each pulse will heat the carbon oil suspension roughly about 5° C.

Each pulse will also heat the skin in general. We have assumed for this qualitative analysis that about ½ of the energy the laser pulse reflects, ¼ is absorbed in the hair ducts and ¼ is absorbed in the skin in general. If we assume that the skin is heated fairly uniformly to a depth of 0.2 cm, a skin density of 1 gm/cm$^3$ and a specific heat for the skin, of 4 J/gm°C. the 0.025 J pulse will heat this typical skin section about 0.04 degrees C. The 60 pulses over about 2 seconds will give a general heating of about 2° C. Therefore, heat deposited generally to the skin is practically negligible.

However, heat from the hot carbon oil suspension will be transferred by conduction to the tissue surrounding the hair duct. I used the following relationship (see note 10 of Zwig & Wibber, IEEE Journal of Quantum Electronics, Vol. QE-23, No. 10 Oct. (1987), Mechanical and Thermal Parameters In Pulsed Laser Cutting of Tissue) to estimate the heat spread from the hot carbon oil suspension in the duct:

$$\delta = /K\tau$$

where $\delta$ represents the thickness of a heated zone during a time $\tau$, K being the heat of conduction. Assuming K=1.44×10$^{-3}$ cm$^2$/S and using 0.03 sec as the time interval between pulses, we estimate that the heat spreads out by about 0.007 cm from the hair duct between each pulse. This is about equal to the radius of the hair duct so we assume that about one half of the temperature rise from each pulse is transferred to the surrounding tissue during the 0.03 second following each pulse. This means that the net increase in the temperature of the carbon-oil suspension from each pulse will be roughly 2.5° C.

Figure 4A:
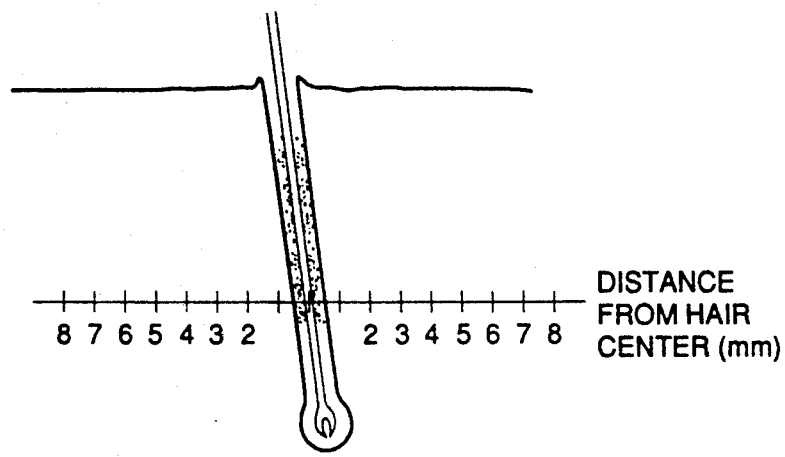
FIGS. 4 A and B show the temperature distribution near a typical hair during the process of a preferred embodiment of the present invention.
Figure 4B:
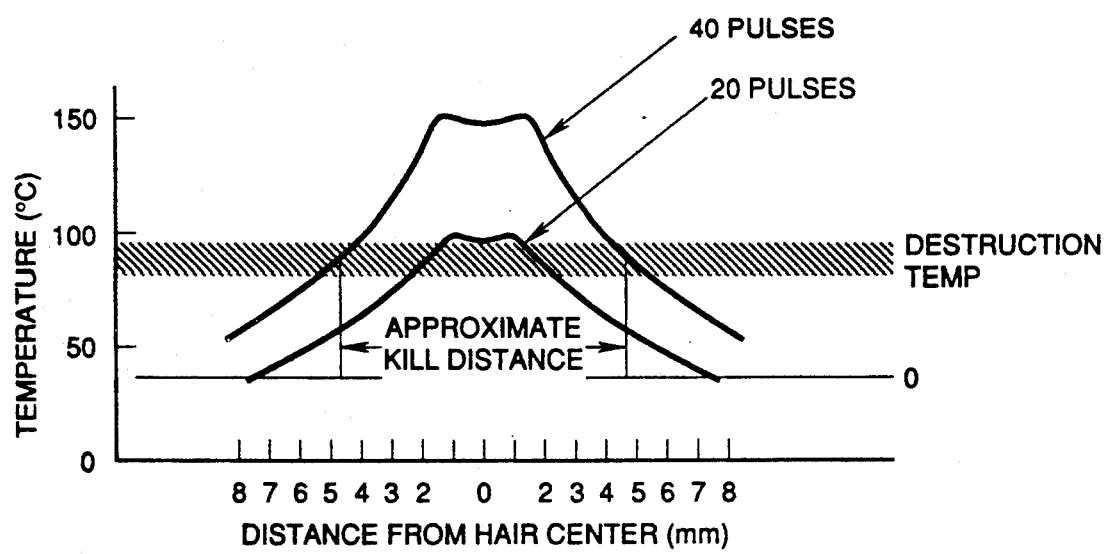

Thus, as depicted in FIG. 4 in about ⅔ second the temperature of the carbon-oil suspension in the hair duct has risen from a normal temperature of 37° C. to about 90° C., a temperature high enough to kill the follicle and the tissue cells immediately surrounding the hair follicle (i.e., within about ±5 hair diameter). In a little more than one second the temperature has risen to about 140° C. which I currently propose as the upper range. At this point the patient would begin to feel pain. Therefore, the illumination should be applied so that no spot is illuminated longer than about one second during one scan. FIGS. 4A and 4B shows a rough approximation of the temperature distribution between ±8 millimeters of the center for a typical hair duct after 20 and 40 pulses.

For my preferred process I illuminate a 10 cm$^2$ area by making 2 or 3 passes over each spot during a 20 second scanning period. For each spot the temperature will have dropped from the range of about 100° C.–140° C. to below about 50° C. during the approximately 7 seconds between scans.

As a result of the illumination, I estimate that essentially all follicles will be killed or will die within 2 weeks because of reduced nourishment due to the destruction of the tissue surrounding the hair duct which feed the follicle. I also estimate that the destroyed tissue is confined to within about 3–6, millimeters (about 6–12 hair diameters) of the center of the hair.

STAIN METHOD

Figure 5:
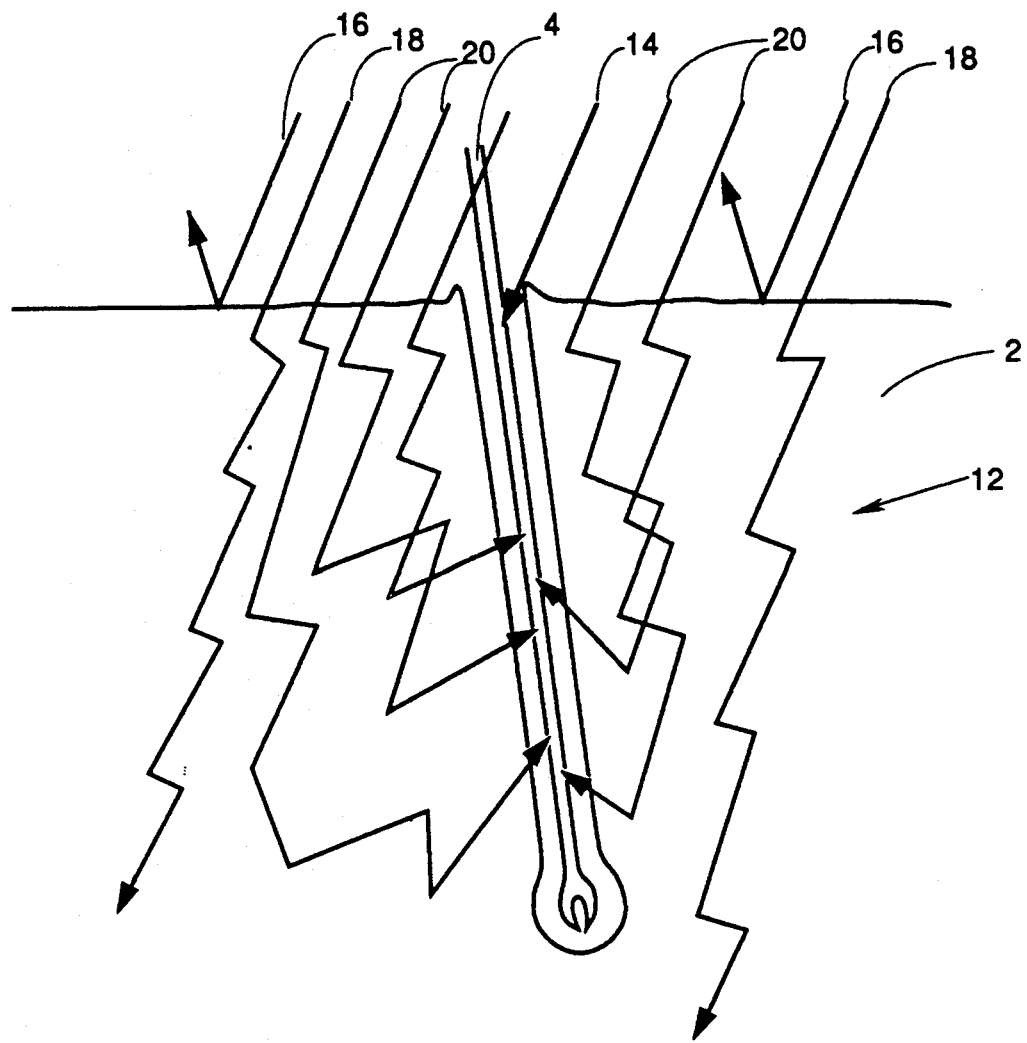
FIG. 5 shows qualitively the paths of the photons of a laser pulse showing absorption in hair dye.

A second embodiment involves the use of dyes to stain the hair follicles. A pulse laser beam of light having a frequency precisely equal to a resonance frequency of the dye illuminates the hair and skin area where the hair is to be removed. The dye and laser beam are chosen so that there is very little absorption by the skin tissue but great absorption by the dye. As indicated in FIG. 5 the photons will undergo diffuse reflection in the skin. But when a photon intersects the hair it is absorbed. Therefore, absorption in the hair could exceed 90%.

To stain the follicles, dye is mixed to form a solution which will penetrate into the follicles. A good substance used to form this solution is hydropertis. In one embodiment, I use commercial hair dye #124 (deep black with blue) which already contains such a solution. It is rubbed on the skin and hair and let stand for 30 minutes. The dye will migrate through the hair all the way to the root.

The skin is cleaned using standard dye removal solution. This dye #124 has an absorption peaks at ~694 nm and ~587 nm which matches perfectly with the wavelength of 587 nm dye laser. Dye #124 also has a resonance of 531 and 584 nm corresponding to the output of copper vapor a laser supplied by Spectra Physics.

For this embodiment I use a pulse width of 150 ns ruby laser and 200 μs dye laser. With a beam cross section diameter of 0.4 cm, the energy density is 2.5–3.5 J/cm$^2$. There are many other dye-laser combinations available which will be obvious to persons skilled in the laser art.

The secret is to match the laser wavelength with a resonance peak in a dye which can be applied to and absorbed in the follicles.

PHOTO CHEMICAL DESTRUCTION

A third embodiment for practicing this invention is to apply a photosensitizer to the hair so that it is absorbed along the full length of the hair to the root. The skin area is then illuminated with laser light which readily penetrates the skin but is absorbed resonantly by the photosensitizer. The photosensitizer undergoes a chemical reaction which is deadly to the hair follicles.

A good specific example of this embodiment of the present invention is to apply a 20% solution of hermotoporphin derivatives topically to the skin over where the hair to be removed has been recently shaved. The solution is absorbed into the portion of the hair remaining under the skin by capillary action. The skin is then cleaned thoroughly with an alcohol pad. Next the skin area is illuminated with an argon dye laser at 632 nm. The energy required is about 5–10 Joules per square centimeter. In this case, the time period is not very important. It could be several minutes per square when the laser energy is absorbed in the hermotoporphin derivatives, singlet oxygen is produced as a result of photochemical reaction. The singlet oxygen is toxic for protein and phosphorlipids in the hair follicles and the follicles are thus killed.

OTHER CONTAMINANT-LASER COMBINATIONS

There are many other chemicals which can be used in the stain method and the photochemical method. I have listed in Table 3 some of these along with a corresponding recommended laser for the illumination.

OTHER EMBODIMENTS

It is very important for all of these embodiments and in other embodiments which will be apparent to persons skilled in the art that the light absorbing substances have a very high absorption coefficient at frequencies which pass readily through the surface of the human skin. An illumination source is matched to this frequency. The substance used can be one with a high resonance peak at the frequency or it can be one with a high broad absorption coefficient over a wide band continuing the illumination frequency. The important thing is to use a light of a frequency which defuses through the skin and has a relatively low absorption in the skin and to use an absorber for contaminating the hair which will provide very high absorption of the light. Persons skilled in the art will recognize that certain frequencies will be preferred for light skinned persons and other frequencies may be preferred for dark skinned persons. The preferred beam size is about 1 square centimeter but could be as large as about 5 square centimeters.

TABLE 3

| Dyes and matching laser. | |
|---|---|
| DYE | LASER |
| Hematoporphyrin derivatives | Argon Dye (632 nm) |
| Indocyanine Green | Diode Laser (785 nm) |
| Microcyanine | Cooper Vapor (540) |
| Photophrin II | Argon Dye (630) |
| Chlorin-E6 | Dye (660) |
| Chlorophyll derivatives | Argon Dye (630) |
| Black Ink | Ruby Laser (694) |

While the above description contains many specifications, the reader should not construe these as limitations on the scope of the invention, buy merely as exemplifications of preferred embodiments thereof. Those skilled in the art will envision many other possible variations are within its scope. Accordingly the reader is requested to determine the scope of the invention by the appended claims and their legal equivalents, and not by the examples which have been given.

I claim:

1. A process for the permanent destruction of plurality of hairs growing on a section of human skin comprising the steps of:
   (a) applying to said hairs and skin section a contaminant having a high absorption of at least one frequency band of light which penetrates human skin,
   (b) cleaning the skin leaving at least a portion of the hairs under the skin contaminated with said contaminant,
   (c) illuminating said skin section with said at least one frequency band of light, a significant portion of which is absorbed in said contaminant so as to permanently destroy said plurality of hairs,
wherein said contaminant is comprised of an oil and absorber suspended in said oil.

2. The process as in claim 1 wherein said absorber is carbon powder.

3. The process as in claim 2 wherein said frequency band of light is produced by a laser.

4. The process as in claim 2 wherein said frequency band of light is a band centered about 10.6 microns (wavelength) and is produced by a $CO^2$ laser.

* * * * *